Feb. 21, 1967 R. S. MOORE Plant Pat. 2,719
ROSE PLANT
Filed Oct. 11, 1965
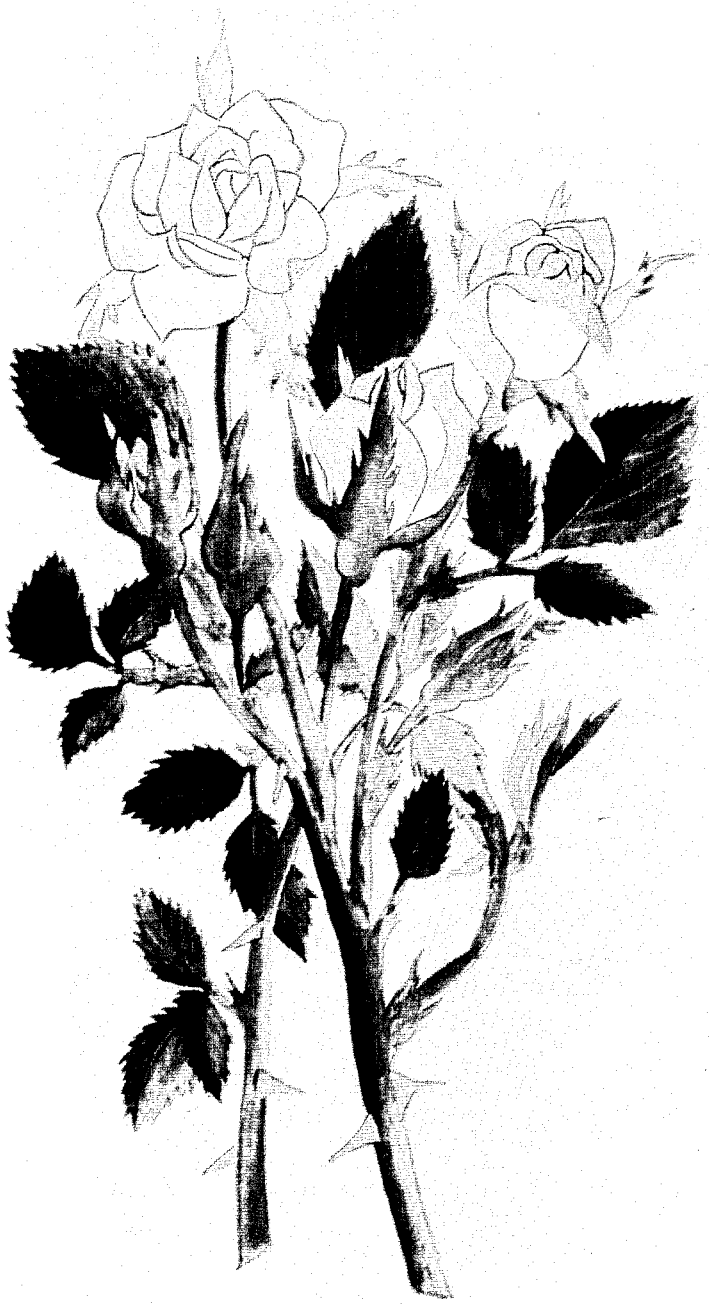
WITNESS
Jeanette Nunn Copley
INVENTOR
Ralph S. Moore United States Patent Office Plant Pat. 2,719
Patented Feb. 21, 1967

2,719
ROSE PLANT

Ralph S. Moore, 2519 E. Mineral King,
Visalia, Calif. 93277

Filed Oct. 11, 1965, Ser. No. 494,994
1 Claim. (Cl. Plt.—5)

The present invention relates to a new and distinct variety of hardy, dwarf, climbing type rose plant of the miniature class; the variety being primarily characterized—as to novelty—by bright red or deep pink (or coral pink) buds with flowers of the same color (which usually deepen as they age), the general color effect being light to medium red.

The variety is further characterized by:

An abundance of bloom, with flowers borne several to the stem in relatively loose clusters or sprays. Moderate fragrance.

A plant which is vigorous, of upright climbing habit, and with dull to semi-glossy, rather large foliage with pointed leaflets; the flowers and foliage being similar in size to the variety Pink Cameo (Plant Patent No. 1,451). The plant, which has an average height of 3½ to 5 feet at maturity can be easily maintained at a lesser height by occasional trimming.

A plant which grows and blooms satisfactorily both in the greenhouse and outdoors; is a good plant for growing in pots; and provides excellent garden decoration as well as cut flowers.

The present variety of miniature rose was originated by me at my nursery located at Visalia, California, under conditions of careful control and observation, as a cross between Little Darling (a floribunda rose, United States Plant Patent No. 1,581) as the seed parent, and Magic Wand (not patented) as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; upright; climbing; seedling, outdoors; cut flowers; garden decoration.
Class: Climbing miniature.
Flowers:
- *Continuity.*—Continuous.
- *Fragrance.*—Moderate.

Flowers borne: Usually in small to medium clusters or sprays (3 to 10) on strong medium length stems.
Quantity of bloom: Abundant.
Bud:
- *Peduncle.*—Medium length; slender, erect; light green; smooth.
- *Before calyx breaks.*—Size—small. Form medium long; pointed; with small foliaceous appendages and numerous tiny, very short hairs on surface of the bud; with foliaceous parts extending beyond the tip of the bud equal to less than ½ of its length.
- *Color.*—Medium green (sometimes lightly tinted bronze).
- *As calyx breaks.*—Color—medium red.
- *As first petal opens.*—Light red with some white at base; size—small.
- *Form.*—Medium length; urn shaped; high centered at first, becoming rounded as it opens.
- *Opening.*—Opens well in all weather.

Bloom: Size when fully open—small, averaging 1½".
- *Petalage.*—Double; 40 to 50 petals (plus several small petaloids); arranged regularly.
- *Form.*—High centered at first with petals rolled loosely outward, and later at maturity being loosely rolled outward and showing open center.

Petals: Fairly thick; satiny both inside and outside.
- *Shape.*—Outside petals oval (broad lanceolate) with rounded tip and wedge shaped base; intermediate—lanceolate with pointed tip and wedge shaped base; inside lanceolate.
- *Color.*—Newly opened flower from plant grown outdoors (September 1965), Visalia, California. Outside petal: Outside surface—Carmine 21/2 with white or pale yellow base; inside surface—Carmine 21/1 or 21/2 with white at base. Intermediate petal: Outside surface—Carmine 21/2 with pale yellow or white base; inside surface—Carmine 21/1 with pale yellow or white at base. Inner petal: Outside surface—Carmine 21/1 with yellow at base; inside surface—Crimson 22 with yellow base.
- *General color effect.*—Newly opened flower—bright medium red. Three days open—same or deeper red (depending upon weather).
- *Behaviour.*—Spent petals drop off.
- *Flower longevity* (September 1965).—Plant in garden 4–5 days. Cut flowers at living room temperature—3 days.

Reproductive organs:
- *Stamens.*—Average; arranged irregularly about pistils; a few mixed with petaloids.
- *Filaments.*—Short to medium (varying length).
- *Anthers.*—Average; yellow.
- *Pollen.*—Average; yellow.
- *Pistils.*—Average.
- *Styles.*—Fairly even; short; bunched.
- *Stigma.*—Pale, greenish.
- *Ovaries.*—All enclosed in calyx.
- *Hips.*—None.
- *Sepals.*—Permanent; spear shaped; recurved.
- *Seeds.*—None.

Foliage:
- *Leaves.*—Compound of seven leaflets (sometimes 5); abundant; moderately leathery; dull to semi-glossy.
- *Leaflets.*—Shape: Lanceolate; apex acute; base rounded acute.
- *Margin.*—Serrate.
- *Color.*—Medium green; new growth sometimes tinted bronze.
- *Rachis.*—Strong, upper surface grooved with few small hairs (nearly smooth); under surface moderately thorny with a few small hairs.
- *Stipules.*—Long, narrow; medium length points, turning out at an angle of about 45 degrees.

Growth:
- *Habit.*—Climbing; upright, much branched.
- *Growth.*—Free; vigorous.
- *Canes.*—Strong; slender.
- *Main stems.*—Color—medium green. Thorns—moderately thorny; oval base; medium length; hooked slightly downward. Color—brown or gray-brown. Prickles—none. Hairs—none.
- *Branches.*—Color medium green. Thorns—moderately thorny; oval base; medium length; hooked slightly downward. Color—brown or gray-brown. Prickles: None. Hairs: None.

*New shoots.*—Color—bright green, often tinted bronze. Thorns—moderately thorny; medium length; hooked downward; medium oval base; color—reddish. Prickles—none. Hairs—none.

The miniature rose plant and its flowers as herein described may vary in slight detail due to climatic, soil and cultural conditions under which the variety may be grown; the present description being of the variety as grown at Visalia, California.

The following is claimed:

A new and distinct variety of miniature rose plant of hardy, upright, much branched, climbing type, as illustrated and described, characterized by buds and flowers resembling the Pink Cameo (Plant Patent No. 1,451) miniature rose in general form but of a distinctly red color, rather than pink, and more double flowers; the general color effect being a bright luminous red; and further characterized by a plant which is vigorous in growth, easy to propagate from cuttings, with more abundant foliage in a brighter shade of green than Pink Cameo, with flowers borne singly and in clusters.

No references cited.

ABRAHAM G. STONE, *Primary Examiner.*

R. E. BAGWILL, *Assistant Examiner.*